United States Patent [19]

Van Overloop

[11] Patent Number: 4,469,463
[45] Date of Patent: Sep. 4, 1984

[54] SCRUB SPONGE WITH PROJECTION AND WELL

[75] Inventor: Ronald R. Van Overloop, Palatine, Ill.

[73] Assignee: The Kendall Company, Boston, Mass.

[21] Appl. No.: 488,571

[22] Filed: Apr. 25, 1983

[51] Int. Cl.³ .................... B43K 5/14; A45D 40/26
[52] U.S. Cl. .................................. 401/134; 401/196; 132/88.7
[58] Field of Search .............. 401/132, 135, 134, 133, 401/196; 222/80, 81, 83, 83.5, 85, 86, 88, 89, 90, 91, 105, 106; 604/1, 2, 3, 403, 408, 416, 244, 411–415; 132/88.7

[56] References Cited

U.S. PATENT DOCUMENTS

| | | | |
|---|---|---|---|
| 2,209,914 | 7/1940 | Gerber et al. | 401/196 |
| 3,248,754 | 5/1966 | Mario | 401/132 |
| 3,636,922 | 1/1972 | Ketner | 401/132 |
| 3,998,559 | 12/1976 | Hoyt | 401/132 |
| 4,027,985 | 6/1977 | Loesser | 401/134 |
| 4,112,944 | 9/1978 | Williams | 604/244 |
| 4,117,841 | 10/1978 | Perrotta | 401/132 |
| 4,148,318 | 4/1979 | Meyer | 401/132 |
| 4,291,697 | 9/1981 | Georgevich | 401/132 |
| 4,330,220 | 5/1982 | Schaar et al. | 401/134 |
| 4,415,288 | 11/1983 | Gordon et al. | 401/132 |

Primary Examiner—Richard J. Apley
Assistant Examiner—Carolyn A. Harrison
Attorney, Agent, or Firm—Powell L. Sprunger

[57] ABSTRACT

A scrub sponge comprising, a packet having a rupturable wall and a closed chamber containing a liquid scrub agent. The sponge has a cover of foam material having a cavity to receive the packet and enclosing the packet. The sponge also has a puncture member intermediate the cover and the packet and having a pair of generally aligned and spaced arms on opposed sides of the packet beneath the cover, and hinge means connecting the arms adjacent one end of the packet. The puncture member has a sharp projection on one of the arms directed toward the packet to pierce the wall when the arms are pressed toward each other to release the scrub agent into the cover. The puncture member has an opening extending through the one arm adjacent the projection. The other arm has a well defining a recess facing toward the packet, with the recess being aligned with the projection.

17 Claims, 8 Drawing Figures

U.S. Patent  Sep. 4, 1984  4,469,463
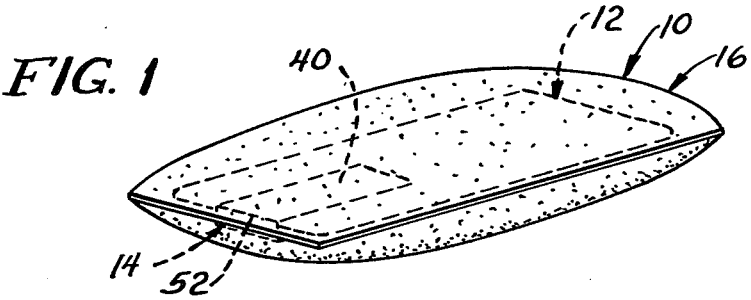
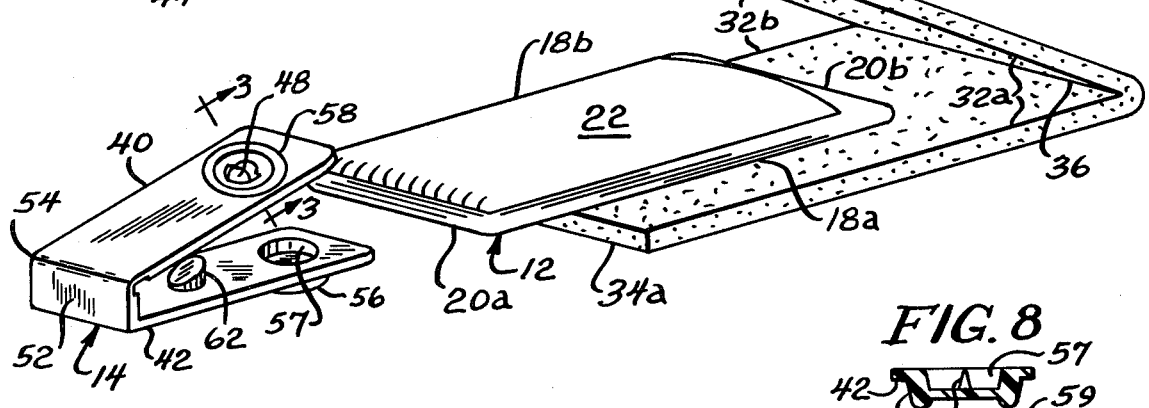
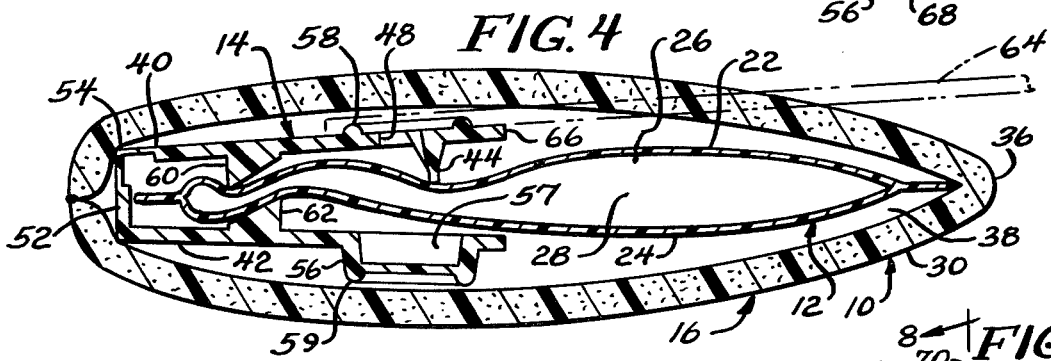
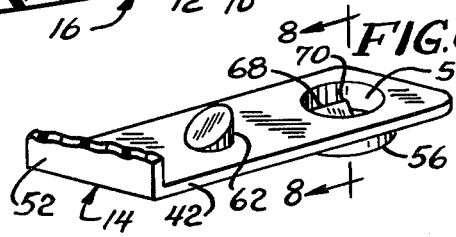
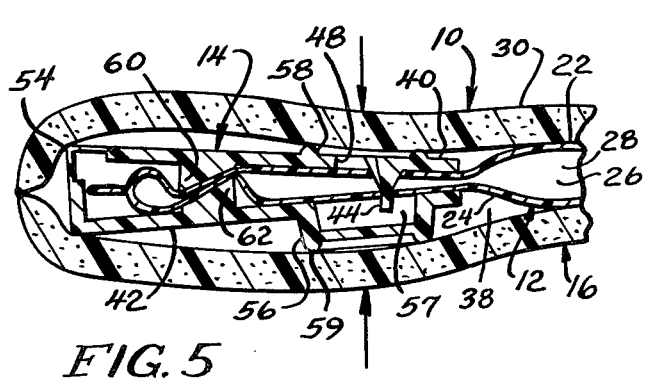
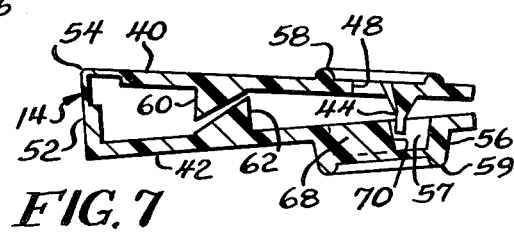

SCRUB SPONGE WITH PROJECTION AND WELL

BACKGROUND OF THE INVENTION

The present invention relates to surgical devices, and more particularly to scrub sponges.

Prior to surgery, the operative site is cleaned by hospital personnel in order to minimize the possibility of contamination around the site. First, a scrub solution comprising a soap or detergent is utilized to wash the patient in the region of the operative site after which the scrub solution is removed from the patient. Next, the patient is painted with an antiseptic liquid, such as povidone iodine, in the region of the site. When dry the antiseptic paint provides a continuous protective film in the region of the site, and surgery is ready to commence.

A scrub sponge is disclosed in U.S. Pat. No. 4,330,220, incorporated herein by reference, which includes a puncture member on one side of a rupturable packet. However, it has been discovered that when a projection on the puncture member pierces the packet it may pass through the sponge and scratch the patient when the sponge is used, which of course is undesirable.

SUMMARY OF THE INVENTION

A principal feature of the present invention is the provision of an improved sponge of simplified construction for scrubbing procedures.

The scrub sponge of the present invention comprises, a packet having a rupturable wall and a closed chamber containing a liquid scrub agent. The sponge has a cover of foam material having a cavity to receive the packet and enclosing the packet. The sponge has a puncture member intermediate the cover and the packet and having a pair of generally aligned and spaced arms on opposed sides of the packet beneath the cover, and hinge means connecting the arms adjacent one end of the packet. The puncture member has a sharp projection on one of the arms directed toward the packet to pierce the wall when the arms are pressed toward each other to release the scrub agent into the cover. The puncture member has an opening extending through the one arm adjacent the projection. The other arm has a well defining a recess facing toward the packet, with the recess being aligned with the projection.

A feature of the present invention is that the projection pierces the puncturable walls when the arms are pressed toward each other.

Another feature of the invention is that the pierced walls release the scrub agent from the packet.

Yet another feature of the invention is that both sides of the packet are ruptured by the opposed arms to release the scrub agent from both sides of the packet.

Still another feature of the invention is that the opening permits passage of the scrub agent into the cover.

Yet another feature of the invention is that the cover retains the scrub agent in a position for easy placement on the patient.

Thus, a feature of the present invention is that the scrub agent may be released and applied to the patient in a simplified manner.

A further feature of the invention is that the well prevents the projection from scratching the patient during use of the sponge.

Yet another feature of the invention is the provision of a boss in the recess to aid in a shearing action of the projection on the packet wall.

Further features will become more fully apparent in the following description of the embodiments of this invention and from the appended claims.

DESCRIPTION OF THE DRAWINGS

In the drawings:

FIG. 1 is a perspective view of a scrub sponge of the present invention;

FIG. 2 is an exploded view of the scrub sponge of FIG. 1;

FIG. 3 is a sectional view taken substantially as indicated along the line 3—3 of FIG. 2;

FIG. 4 is a sectional view illustrating the sponge prior to puncture of a packet in the sponge;

FIG. 5 is a fragmentary sectional view illustrating the sponge after the packet has been pierced by a puncture member;

FIG. 6 is a fragmentary perspective view of another embodiment of a puncture member of the present invention;

FIG. 7 is a sectional view of the puncture member of FIG. 6 showing arms as pressed toward each other; and FIG. 8 is a sectional view taken substantially as indicated along the line 8—8 of FIG. 6.

DESCRIPTION OF THE PREFERRED EMBODIMENTS

Referring now to FIGS. 1-4, there is shown a scrub sponge generally designated 10 having a packet 12, a puncture member 14, and a cover 16. The packet 12 has a pair of side edges 18a and 18b, and a pair of end edges 20a and 20b connecting the side edges 18a and b. The packet 12 has a front wall 22 and a back wall 24 which are joined at their periphery to define a chamber 26 intermediate the front and back walls 22 and 24. The front and back walls 22 and 24 are made from a puncturable material, such as a lamination of metallic foil and heat sealable plastic, such that the edges of the front and back walls 22 and 24 may be heat sealed together to form the chamber 26. The packet 12 contains a liquid scrub agent 28 in the chamber 26, such as a solution of soap or detergent with or without povidone iodine, or a solution containing an antiseptic agent, such as povidone iodine.

The cover 16 preferably comprises an absorbent and porous foam material, such as polyurethane foam. In a preferred form, the cover 16 comprises an elongated strip 30 having a pair of side edges 32a and 32b, and a pair of end edges 34a and 34b connecting the side edges 32a and b. The strip 30 is folded about a fold line 36 at a longitudinal central portion of the strip, such that the end edges 34a and 34b are located adjacent each other when the strip 30 is folded. The side edge 32a of the strip 30 intermediate fold line 36 and the end edges 34a and b are joined together by suitable means, such as by heat sealing, the side edge 32b intermediate the fold line 36 and the end edges 34a and b are joined together by suitable means, such as by heat sealing, and the end edges 34a and b are joined together by suitable means, such as by heat sealing. In this manner, the joined edges of the strip 30 define a cavity 38 to receive the packet 12, with the width of the packet between the side edges 18a and b being approximately equal to the width of the cavity 38, and with the length of the packet 12 intermediate the end edges 20a and b being approximately equal to the length of the cavity 38. In this configuration, the side edge 18a of the packet 12 is located adjacent the side edge 32a of the cover 16, the side edge 18b of the packet 12 is located adjacent the side edge 32b of the cover 16, the end edge 20a of the packet 12 is located adjacent the joined end edges 34a and b of the cover 16, and the end edge 20b of the packet 12 is located adjacent the fold line 36 of the cover 16.

The puncture member 14 may be formed from a flexible plastic material, such as polypropylene. As shown, the puncture member 14 is located intermediate the cover 16 and the packet 12. The puncture member 14 has a pair of generally aligned and spaced arms 40 and 42 on opposed sides of the packet 12 beneath the cover 16. The arm 40 has a sharp projection 44 directed toward the packet 12. The arm 40 has an opening 48 extending through the arm 40 and located adjacent the projection 44. The puncture member 14 has a hinge 52 connecting one end of the arms 40 and 42 with the hinge 52 having a lateral flexible region 54 of reduced thickness adjacent the arm 40 to permit movement of the arms 40 and 42 toward each other. The projection 44 is tapered to a sharp point for a purpose which will be described below. As shown, the arm 40 may have a raised ring 58 surrounding the opening 48, and the arm 42 may have a raised ring 59, such that the user may feel the rings 58 and 59 through the cover 16 in order to locate the region of the projection 44 and the opening 48.

The arm 42 has a well 56 defining a recess 57 facing toward the packet 12. As shown, the recess 57 is aligned with the projection 44.

The arm 40 has an alignment boss 60 intermediate the projection 44 and hinge 52, and the arm 42 has an alignment boss 62 intermediate the well 56 and the hinge 52. The bosses 60 and 62 are aligned with each other, and have an oppositely directed tapered surface facing toward the packet 12. Also, the bosses 60 and 62 nearly engage when the arms 40 and 42 are pressed toward each other.

With reference to FIG. 4, the arms 40 and 42 are located on opposed sides of the packet 12, and the hinge 52 is located adjacent one end of the packet 12. The arms 40 and 42 are located in a first spaced position such that the projection 44 does not pierce the packet 12 prior to use of the sponge 10. Also, in this configuration, the bosses 60 and 62 are spaced from each other. However, with reference to FIG. 5, when it is desired to use the sponge 10, the arms 40 and 42 are pressed toward each other to a second close position. In this configuration, the bosses 60 and 62 guide the projection 44 into the well 56 to pierce the opposed walls of the packet 12. After the walls have been pierced, the scrub agent 28 passes through the walls on opposed sides of the packet 12 and through the opening 48 into the cover 16 in order to impregnate the cover 16 for use of the sponge 10 on a patient. When the arms 40 and 42 are pressed to their second close position, the projection 44 is received in the recess 57, and the well 56 prevents the projection 44 from passing through the arm 42 in order to prevent scratching of the patient during use of the sponge 10 by the projection 44.

In accordance with the present invention, a scrub sponge 10 may be used with an agent 28 which may be either detergent or povidone iodine mixed with the detergent in order to initially scrub the site of surgery for a quick kill of bacteria in the region of the site. Also, the sponge 10 may be utilized with an agent 28 of povidone iodine in order to paint the surgery site after the scrub has been completed for a long term kill of bacteria in the site. For this procedure, with reference to FIG. 4, the sponge 10 preferably has an elongated handle 64 extending from an outer end 66 of the arm 40 and passing through an opening in the cover 16 in order to hold the sponge 10 by the handle 64 while performing the paint procedure.

Another embodiment of the puncture member 14 of the present invention is illustrated in FIGS. 6–8 in which like reference numerals designate like parts. In this embodiment, the well 56 has a raised boss 68 having an outer edge 70 located adjacent the projection 44 when the arms 40 and 42 are pressed toward each other. The boss 68 aids in performing a shearing action by the projection 44 through the packet walls when the arms 40 and 42 are pressed toward each other. In other respects, the puncture member 14 of FIGS. 6–8 is similar to the puncture member 14 described in connection with FIGS. 1–5.

The foregoing detailed description is given for clearness of understanding only, and no unnecessary limitations should be understood therefrom, as modifications will be obvious to those skilled in the art.

I claim:

1. A scrub sponge, comprising:
   a packet having a rupturable wall and a closed chamber containing a liquid scrub agent;
   a cover of foam material having a cavity to receive said packet and enclosing said packet; and
   a puncture member intermediate said cover and the packet and having a pair of generally aligned and spaced arms on opposed sides of the packet beneath the cover, hinge means connecting said arms adjacent one end of the packet, a sharp projection on one of the arms directed toward the packet to pierce the wall when the arms are pressed toward each other to release the scrub agent into the cover, well means on the other of the arms defining a recess facing toward the packet aligned with and adapted to receive said projection thereby preventing said projection from protruding through said other arm and scratching the patient, and alignment means on each of said arms to guide said projection into said recess when the arms are pressed toward each other.

2. The sponge of claim 1 wherein said cover comprises an elongated sheet having a pair of opposed side edges and a pair of opposed end edges connecting the side edges, with said sheet being folded along a line at a longitudinal central portion of the sheet intermediate said end edges, said side edges intermediate the fold line and end edges being joined together, and said end edges being joined together to define the cavity.

3. The sponge of claim 2 wherein said packet has a pair of opposed side edges, and a pair of opposed end edges connecting the side edges, with one of the packet end edges being located adjacent the joined end edges of the cover, with the other packet end edge being located adjacent the cover fold line, and with the packet side edges being located adjacent the joined side edges of the cover.

4. The sponge of claim 1 wherein said cover comprises a polyurethane foam.

5. The sponge of claim 1 wherein the walls of said packet comprise a metallic foil.

6. The sponge of claim 1 wherein said scrub agent comprises povidone iodine.

7. The sponge of claim 1 wherein said scrub agent comprises a detergent.

8. The sponge of claim 1 wherein said puncture member comprises a flexible plastic material.

9. The sponge of claim 1 wherein said projection is tapered toward a relatively sharp point.

10. The sponge of claim 1 wherein said packet has a width and length substantially the width and length of said cavity.

11. The sponge of claim 1 including an elongated handle extending from the puncture member through the cover.

12. The sponge of claim 11 wherein the handle extends from an end of one of the arms.

13. The sponge of claim 1 wherein the hinge means includes a lateral flexible region of reduced thickness adjacent one of the arms.

14. The sponge of claim 1 wherein the one arm has an opening extending therethrough adjacent the projection.

15. The sponge of claim 14 including a raised ring extending around the opening on a surface of the one arm remote the packet.

16. The sponge of claim 1 including a raised boss in the well having an outer edge located adjacent the projection when the arms are pressed toward each other.

17. The sponge of claim 1 wherein said alignment means comprises an alignment boss on each of the arms intermediate the projection and well and the hinge means, said bosses being aligned and having an oppositely directed tapered surface facing toward the packet, and said bosses nearly engaging when the arms are pressed toward each other.

* * * * *